US008883189B2

(12) United States Patent
Olson (10) Patent No.: US 8,883,189 B2
(45) Date of Patent: Nov. 11, 2014

(54) INTRAOCULAR ENCAPSULATION OF OXYGENIC BACTERIA

(71) Applicant: Jeffrey Olson, Cherry Hills, CO (US)

(72) Inventor: Jeffrey Olson, Cherry Hills, CO (US)

(73) Assignee: The Regents of the University of Colorado, a Body Corporate, Denver, CO (US)

( * ) Notice: Subject to any disclaimer, the term of this patent is extended or adjusted under 35 U.S.C. 154(b) by 0 days.

(21) Appl. No.: 14/239,955

(22) PCT Filed: Sep. 26, 2012

(86) PCT No.: PCT/US2012/057195
§ 371 (c)(1),
(2), (4) Date: Feb. 20, 2014

(87) PCT Pub. No.: WO2013/049107
PCT Pub. Date: Apr. 4, 2013

(65) Prior Publication Data
US 2014/0294914 A1    Oct. 2, 2014

Related U.S. Application Data

(60) Provisional application No. 61/539,858, filed on Sep. 27, 2011.

(51) Int. Cl.
*A61F 2/14* (2006.01)
*A61F 9/00* (2006.01)
*A61K 35/74* (2006.01)
*A61K 9/48* (2006.01)

(52) U.S. Cl.
CPC ............. *A61K 9/4816* (2013.01); *A61F 9/0017* (2013.01); *A61K 35/74* (2013.01)
USPC ........................................................ 424/427

(58) Field of Classification Search
None
See application file for complete search history.

(56) References Cited

U.S. PATENT DOCUMENTS

| 2005/0288619 | A1 | 12/2005 | Gharib et al. |
| 2008/0089923 | A1 | 4/2008 | Burkstrand et al. |
| 2010/0040670 | A1* | 2/2010 | Odrich et al. ................. 424/427 |

FOREIGN PATENT DOCUMENTS

WO     2007130945     11/2007

OTHER PUBLICATIONS

International Preliminary Report on Patentability for PCT/US2012/057195 dated Apr. 1, 2014.
International Search Report and Written Opinion dated Mar. 13, 2013 in Application No. PCT/US2012/057195.

* cited by examiner

*Primary Examiner* — Anand Desai
*Assistant Examiner* — Melissa Mercier
(74) *Attorney, Agent, or Firm* — Snell & Wilmer L.L.P.

(57) ABSTRACT

Exemplary embodiments comprise an implantable ophthalmic device comprising at least one shell encapsulating oxygenic bacteria and growth medium and designed to increase the oxygen partial pressure in an oxygen-deprived structure of, or space within, an eye. Exemplary embodiments may be used therapeutically to treat ischemic retinopathies in situ and thereby prevent damage, for example, retinal damage.

9 Claims, 10 Drawing Sheets

INTRAOCULAR ENCAPSULATION OF OXYGENIC BACTERIA

CROSS-REFERENCE TO RELATED APPLICATIONS

This application is U.S. national phase filing under 35 U.S.C. §371 of PCT/US2012/057195 filed on Sep. 26, 2012, which claims priority from U.S. Provisional Application No. 61/539,858 filed on Sep. 27, 2011, both of which are incorporated herein by reference.

BACKGROUND

Ischemic retinopathies, such as diabetic retinopathy, macular degeneration, glaucoma, retinopathy of prematurity, retinal venous and arterial occlusions, among others, comprise a major leading cause of vision loss in the industrialized world. The fundamental underlying problem associated with these ischemic retinopathies is a chronic shortage of oxygen delivery to the retina. Over time, the cells in the retina progressively lose their ability to function, and the patient suffers a progressive loss of vision. While the current state of treatment using either lasers or injectable medication provides a means of slowing the rate of vision loss, it does not treat the underlying problem, i.e., a lack of tissue oxygen.

What is therefore needed is a novel intraocular implant that would make possible the reversal of ischemic retinopathies and the associated vision loss. The present disclosure addresses this need.

SUMMARY

Exemplary embodiments comprise an implantable ophthalmic device designed to increase the oxygen concentration (i.e., partial pressure) in an oxygen-deprived structure of, or space within, an eye. An exemplary implantable ophthalmic device comprises at least one shell encapsulating oxygenic bacteria and growth medium. Exemplary methods are also disclosed and may comprise implanting one or a plurality of exemplary implantable ophthalmic devices. Exemplary embodiments may be used therapeutically to treat ischemic retinopathies in situ and thereby prevent damage, for example, retinal damage.

BRIEF DESCRIPTION OF THE DRAWINGS

The accompanying drawings are included to provide a further understanding of the disclosure and are incorporated in and constitute a part of this specification, illustrate embodiments of the disclosure, and together with the description serve to explain the principles of the disclosure.

DETAILED DESCRIPTION

Persons skilled in the art will readily appreciate that various aspects of the present disclosure may be realized by any number of methods and apparatuses configured to perform the intended functions. Stated differently, other methods and apparatuses may be incorporated herein to perform the intended functions. It should also be noted that the accompanying drawing figures referred to herein are not all drawn to scale, but may be exaggerated to illustrate various aspects of the present disclosure, and in that regard, the drawing figures should not be construed as limiting. Finally, although the present disclosure may be described in connection with various principles and beliefs, the present disclosure should not be bound by theory.

Figure 1:
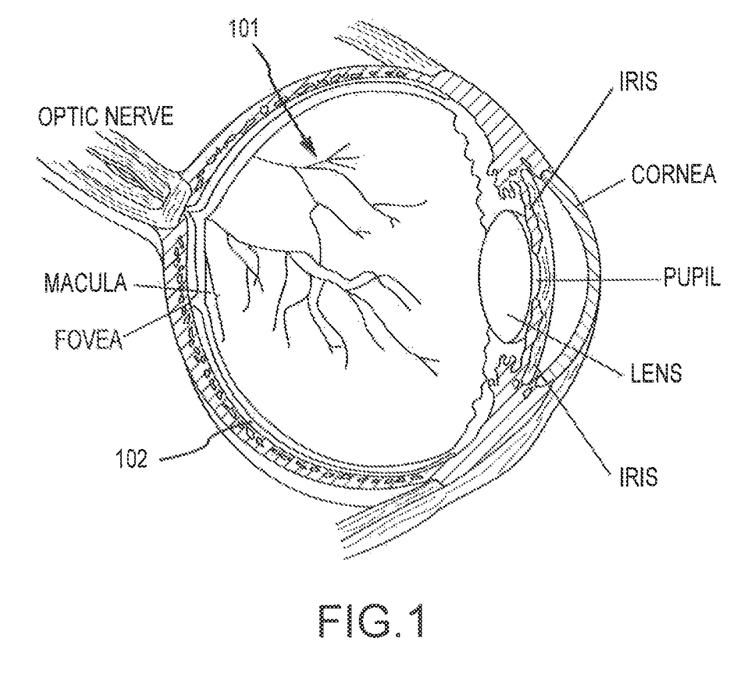
FIG. 1 illustrates a cross-section showing the anatomy of the human eye.

With reference to FIG. 1, exemplary embodiments comprise an implantable ophthalmic device designed to increase the oxygen concentration (i.e., partial pressure) in a vitreous cavity 101 of an eye. As a result, exemplary embodiments may enhance oxygen delivery to an oxygen-deprived structure of, or space within, an eye, for example, a retina 102. Exemplary embodiments may be used therapeutically to treat ischemic retinopathies in situ and thereby prevent damage, for example, retinal damage.

Figure 2:
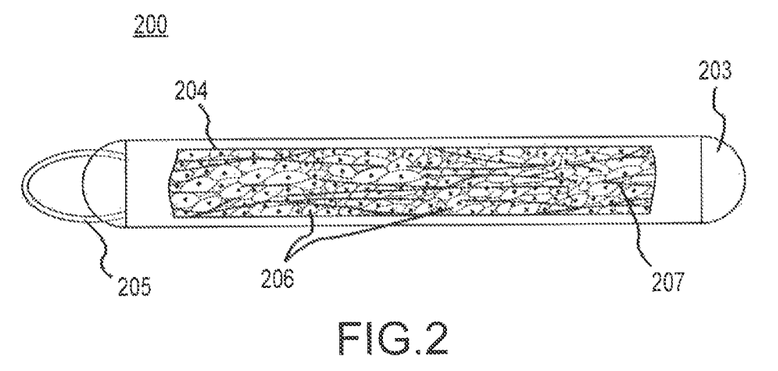
FIG. 2 illustrates an exemplary implantable ophthalmic device.

With reference to FIG. 2, an exemplary implantable ophthalmic device 200 comprises at least one shell 203, oxygenic bacteria 206, and growth medium 207. In one exemplary embodiment shell 203 encapsulates both oxygenic bacteria 206 and growth medium 207. In various exemplary embodiments, implantable ophthalmic device 200 is configured to provide additional oxygen to an oxygen-deprived structure of, or space within, an eye.

Shell 203 is generally any biocompatible structure configured to prevent immune cells from reaching the interior of the implantable ophthalmic device, and also prevent oxygenic bacteria from migrating outward. Stated another way, shell 203 may comprise any structure configured to confine oxygenic bacteria while releasing oxygen produced by the oxygenic bacteria and while keeping immune cells out of contact with the oxygenic bacteria. The shell may have any shape, be any suitable size, and comprise any biocompatible material.

Exemplary shapes of shell 203 include spherical, cylindrical tubular, elongate tubular, a capsule, a coil, cubical, conical, frustoconical, toroidal, etc. In exemplary embodiments, a shape having a smaller crossing profile is selected. In exemplary embodiments, it may be desirable to maximize both surface area for gas exchange and light absorption. In other exemplary embodiments, the shape of a shell of an implantable ophthalmic device intended for longer use may have a smaller surface-area-to-volume ratio to encapsulate more oxygenic bacteria in a smaller space. In still other exemplary embodiments, the shape of a shell of an implantable ophthalmic device intended for shorter use may have a larger surface-area-to-volume ratio to expose more oxygenic bacteria to an oxygen-deprived structure or space.

The size of shell 203 may be selected to encapsulate a desired amount of oxygenic bacteria and growth medium. In various embodiments, the shell has a volume of from about 50 µL to about 500 µL, more preferably from about 200 µL to about 300 µL, most preferably about 250 µL. In various embodiments, the shell has an internal diameter of from about 0.1 mm to about 4 mm, more preferably from about 0.2 mm to about 1 mm, or about 0.75 mm. In various embodiments, the shell has a length of from about 1 mm to about 10 mm, more preferably from about 1 mm to about 7 mm, or about 5 mm. The size and length may be selected so as to not impinge the vision of a patient when implanted in a vitreous cavity of his/her eye.

Generally speaking, shell 203 may comprise any biocompatible, immunologically inert material(s). More specifically, the shell may comprise a rigid material, such as plastics, metals, alloys and the like, or a flexible material, such as silicones, nitriles, nylons, polycarbonates, polyethylenes, polypropylenes and the like. The material of all or only a portion of the shell may be completely or semi-transparent or translucent to allow the passage of light to a space within the shell to thereby allow light absorption by oxygenic bacteria. An exemplary shell may comprise a plurality of materials.

With continued reference to FIG. 2, in exemplary embodiments, shell 203 comprises a porous membrane 204 or other material that is porous. In exemplary embodiments, a portion of the shell (e.g., a central portion, one or more bands about the shell, one or more "windows" through the shell, etc.) comprises a porous membrane 204 or other material that is porous. As used herein, the term "porous" generally refers to being permeable to a reactant necessary to drive, or a product that results from, a chemical reaction by which oxygenic bacteria generate oxygen. By way of non-limiting example, a porous membrane may be configured to allow the passage of gases (e.g., oxygen and carbon dioxide exchange) and to prevent immune cells from reaching the interior of the implantable ophthalmic device, and also prevent oxygenic bacteria from migrating outward.

Exemplary porous materials for use in connection herewith may comprise various filtration membranes known in the art, including NF-90 nanopore membranes and biologically inert reconstituted cellulose membranes (e.g., micro-dialysis hollow bore membranes). Still additional porous materials can comprise one or more of poly (vinylidene fluoride) (PVDF), nylon, regenerated cellulose, dialysis tubing, osmosis/reverse osmosis membranes, biotissues (e.g., amniotic membrane, lens capsule, Bruch's membrane, etc.), and the like. Exemplary porous materials may have an average pore size of from about 1 kDa to about 50 kDa, more preferably from about 10 kDa to about 20 kDa, most preferably from about 13 kDa to about 18 kDa.

With continued reference to FIG. 2, in exemplary embodiments, shell 203 comprises an anchor 205 (e.g., a suture clip or the like comprising any suitable material) designed to secure the implantable ophthalmic device during and/or after implantation. In exemplary embodiments, anchor 205 secures the implantable ophthalmic device to an adjacent tissue or structure (e.g., via a suture). In exemplary embodiments, anchor 205 secures a plurality of shells together, for example, a plurality of shells arranged in parallel (e.g., a bundle of elongate tubular shells). In yet other exemplary embodiments, anchor 205 secures a plurality of exemplary implantable ophthalmic devices together.

In exemplary embodiments, shell 203 is all or partially coated with a therapeutic agent, such as a drug, antiproliferative, antithrombotic, etc. Such embodiments may be especially advantageous when an exemplary implantable ophthalmic device is not implanted in a vitreous cavity of an eye but at or near another oxygen-deprived structure of, or space within, an eye, such as an anterior chamber or under conjunctiva, to name just a few.

With reference again to FIG. 2, oxygenic bacteria 206 generally includes any and all bacteria which generate oxygen, including photosynthetic bacteria, such as cyanobacteria, also known as blue-green algae (e.g., *Synechococcus* sp.) and others, which convert carbon dioxide and water into carbohydrate and oxygen in the presence of light according to the following formula—$CO_2$ (carbon dioxide)+$H_2O$ (water) =$CH_2O$ (carbohydrate)+$O_2$ (oxygen). In general, any suitable type/species of oxygen producing bacteria can be used in accordance with the present disclosure.

In various embodiments, instead of using the entire bacteria, only the cellular machinery that produces oxygen is used. In other embodiments, normal human cells (e.g., RPE cells) could be used and spliced in the DNA from the bacteria (or its cellular machinery) to allow those cells to produce oxygen, still referred to herein as oxygenic bacteria.

An exemplary amount of oxygenic bacteria 206 is generally that sufficient to generate enough local oxygen to increase the oxygen partial pressure at or near an oxygen-deprived structure of, or space within, an eye, by at least 2 mmHG, 4 mmHg or more, preferably to an otherwise "normal" range. A normal range, in accordance with various embodiments, may be at least about 16 mmHg, more preferably at least about 18 mmHg, most preferably about 20 mmHg, or an otherwise normal or improved oxygen partial pressure.

With continued reference to FIG. 2, growth medium 207 generally includes any structure or chemical configured to enhance growth of oxygenic bacteria within the implantable ophthalmic device. For instance, a growth medium may comprise a surface such as a scaffold, an oxygenic bacteria nutrient, and/or a reactant necessary to drive a chemical reaction by which oxygenic bacteria generate oxygen.

An exemplary amount of growth medium 207 is generally that sufficient to support an amount of oxygenic bacteria sufficient to increase the oxygen partial pressure at or near an oxygen-deprived structure of, or space within, an eye, by at least 1 mmHg, 2 mmHg, 4 mmHg or more, preferably to an otherwise "normal" range. A normal range, in accordance with various embodiments, may be at least about 16 mmHg, more preferably at least about 18 mmHg, most preferably about 20 mmHg, or an otherwise normal or improved oxygen partial pressure.

In various embodiments, a portion of an implantable ophthalmic device rests outside the eye, for example to be used as a reservoir.

In various embodiments, an implantable ophthalmic device comprises a long, thin, hollow tube membrane which is twisted and/or braided on itself, but comprises one continuous lumen.

Figure 6:
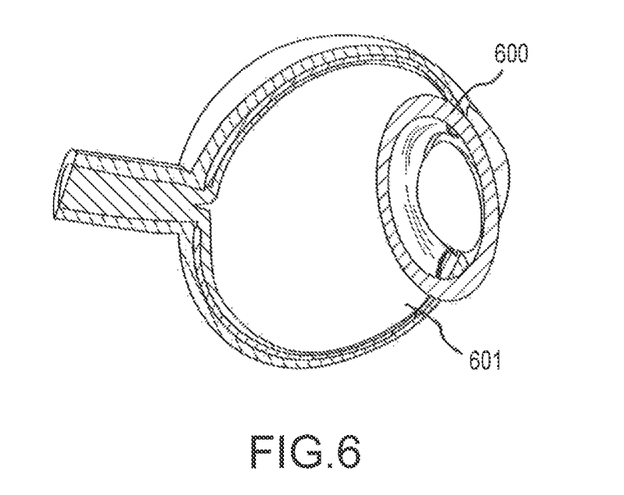
FIG. 6 illustrates still another exemplary implantable ophthalmic device.

In other embodiments, and with reference to FIG. 6, an implantable ophthalmic device 600 is placed circumferentially around the pars plana, and inside the vitreous cavity 601. This embodiment can facilitate a much larger device (e.g., up to or greater than 75 mm for a circumferential implant having a 12 mm radius).

Figure 7:
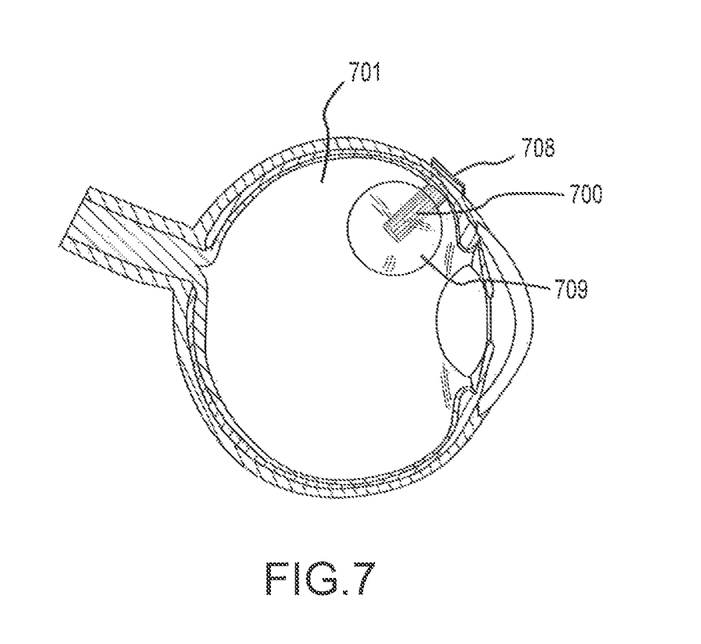
FIG. 7 illustrates an exemplary implantable ophthalmic device comprising a plug.

In yet other embodiments, and with reference to FIG. 7, an implantable ophthalmic device 700 could be configured as a plug 708 placed thru the sclera, with an expandable balloon type membrane 709 inside the vitreous cavity 701. In such embodiments, a small gauge needle can pierce the roof of plug 708 to inject the oxygenic bacteria solution into expandable balloon type membrane 709, comprised of a porous material. Such embodiments would allow device 700 to stay in place, and the oxygenic bacteria could be removed and/or switched out with a fresh colony as needed.

In still other embodiments, an intraocular lens could be modified to be an implantable ophthalmic device.

Figure 3:
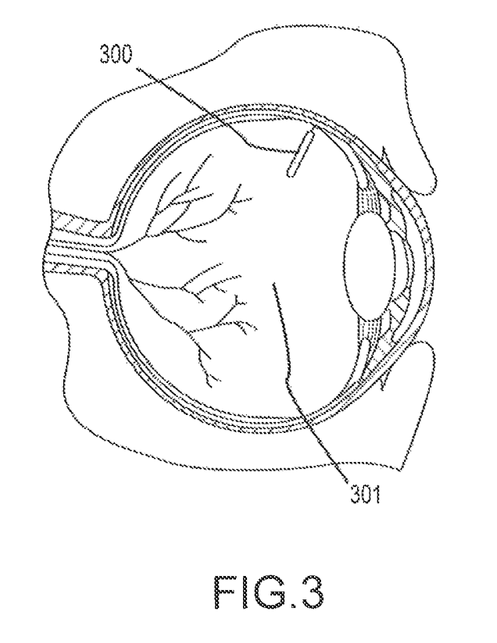
FIG. 3 illustrates a cross-section showing an exemplary implantable ophthalmic device implanted in a vitreous cavity of an eye.

Exemplary methods comprise delivering and implanting one or a plurality of exemplary implantable ophthalmic devices. In various embodiments, and with reference to FIG. 3, an exemplary implantable ophthalmic device 300 is implanted in a vitreous cavity 301 of an eye or another space that receives natural ambient light such that an internal light supply is not required to drive a photosynthetic reaction. In general however, an exemplary implantable ophthalmic device may be implanted at or near any oxygen-deprived structure of, or space within, an eye, such as an anterior chamber or under conjunctiva, or in the wall of a membrane, to name just a few.

Surgical access to an oxygen-deprived structure or space may be accomplished according to methods known in the art, for example, through a pars plana incision.

Exemplary methods also comprise anchoring an exemplary implantable ophthalmic device at or near an oxygen-deprived structure of, or space within, an eye. The step of anchoring may comprise suturing, clipping, tying or the like. In exemplary embodiments, the step of anchoring may comprise anchoring an exemplary implantable ophthalmic device in the periphery of a vitreous cavity of a patient's eye so as to not impinge her/his vision.

Exemplary methods further comprise increasing the oxygen partial pressure at or near an oxygen-deprived structure of, or space within, an eye by at least about 1%, more preferably at least about 5%, most preferably at least about 10%. Exemplary methods further comprise increasing the oxygen partial pressure at or near an oxygen-deprived structure of, or space within, an eye by at least 1 mmHg, 2 mmHg, 4 mmHg or more, to at least about 16 mmHg, more preferably at least about 18 mmHg, most preferably about 20 mmHg, or an otherwise normal or improved oxygen partial pressure. Exemplary methods still further comprise increasing the oxygen partial pressure at or near an oxygen-deprived structure of, or space within, an eye for at least about 2 weeks, more preferably at least about 3-6 months, most preferably at least about 1 year.

Figure 4:
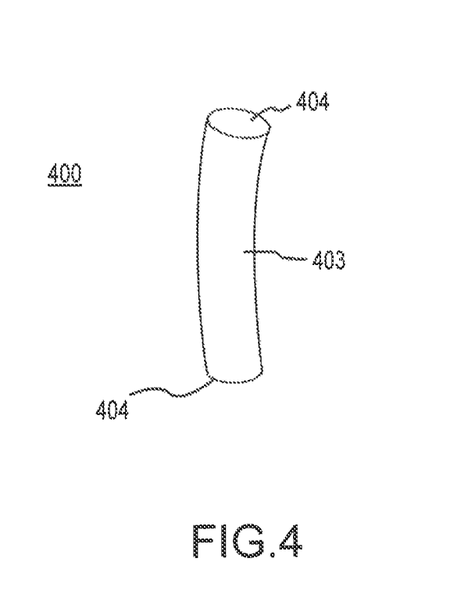
FIG. 4 illustrates another exemplary implantable ophthalmic device.

Exemplary embodiments of various implantable ophthalmic devices were constructed and tested. With reference to FIG. 4, an exemplary implantable ophthalmic device 400 was constructed comprising a cylindrical tubular shell 403 capped on both ends with a porous membrane 404 and filled with *Synechococcus* sp. oxygenic bacteria. Cylindrical tubular she 403 comprises a biocompatible, immunologically inert clear polymer. Porous membranes 404 comprise NF-90 nanopore membranes.

Figure 5:
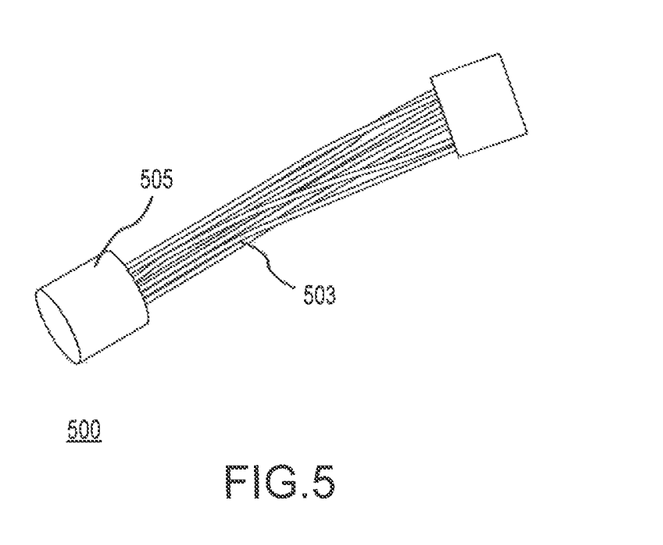
FIG. 5 illustrates yet another exemplary implantable ophthalmic device.

With reference to FIG. 5, another exemplary implantable ophthalmic device 500 was constructed comprising a bundle of elongate tubular shells 503 filled with *Synechococcus* sp. oxygenic bacteria and secured with endcap 505 which may further comprise an anchor. Elongate tubular shells 503 comprise micro-dialysis hollow bore, reconstituted cellulose membranes having an average pore size of 13 kDa.

Figure 8:
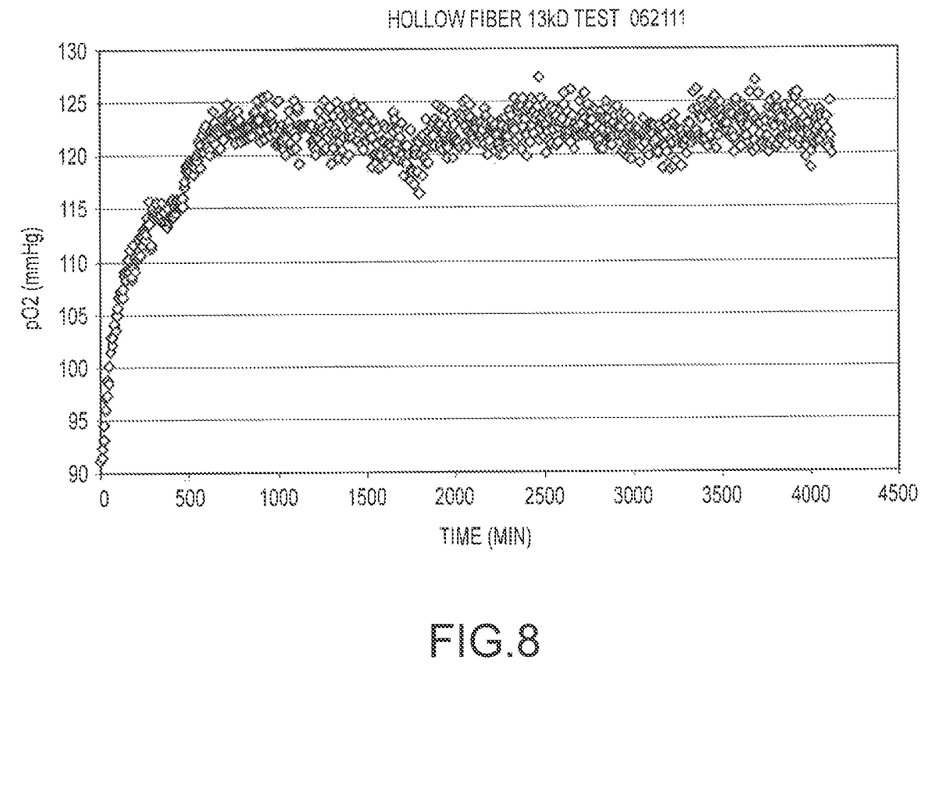
FIG. 8 depicts the oxygen partial pressure measured from *Synechococcus* sp. cells submerged in a balanced salt solution as a function of time.

With reference to FIG. 8, using an exemplary implantable ophthalmic device such as that described with reference to FIG. 5, relatively high levels of oxygen generation were measured, similar to those found with unencapsulated organisms. In particular, FIG. 8 depicts the oxygen partial pressure (pO2) measured from *Synechococcus* sp, cells submerged in a balanced salt solution as a function of time. It was observed that within approximately 500 minutes, the oxygen partial pressure was above 120 mmHg.

In other testing, oxygen at a statistically significant higher rate was produced for over 165 days. Optical density showed that the culture was in an exponential phase of growth after 4 months.

Figure 9:
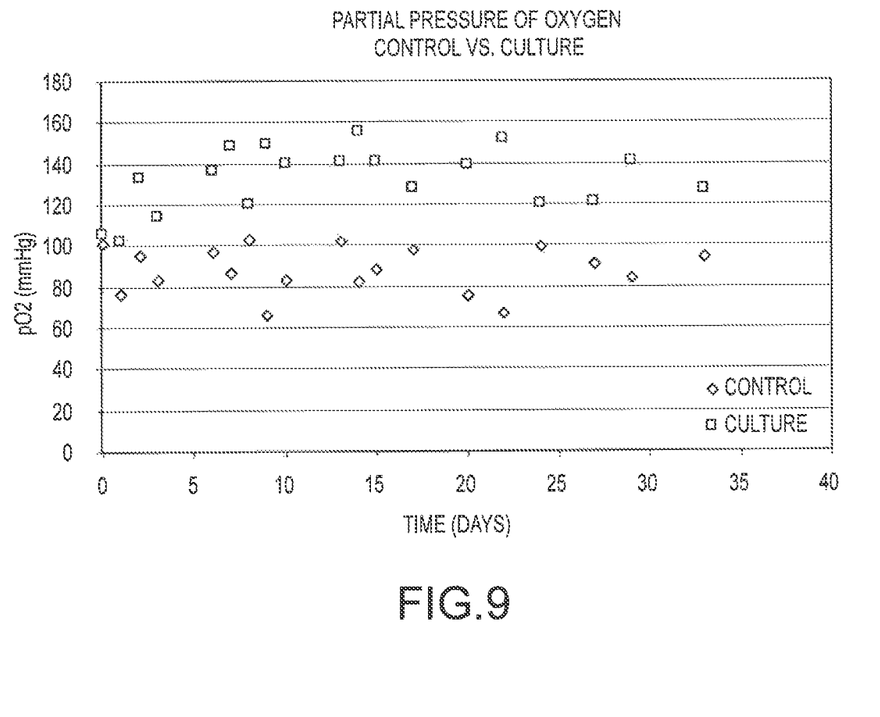
FIG. 9 depicts the oxygen partial pressure measured in a control flask and a culture flask containing growth medium and *Synechococcus* sp. cells as a function of time.

Laboratory testing was conducted to evaluate *Synechococcus* sp. Cells. FIG. 9 depicts the oxygen partial pressure (pO2) measured in a control flask (contained only growth medium) and a culture flask (contained growth medium and *Synechococcus* sp. cells) as a function of time. This test demonstrates the capacity of *Synechococcus* sp. cells to generate local oxygen within an oxygen-deprived space.

Figure 10:
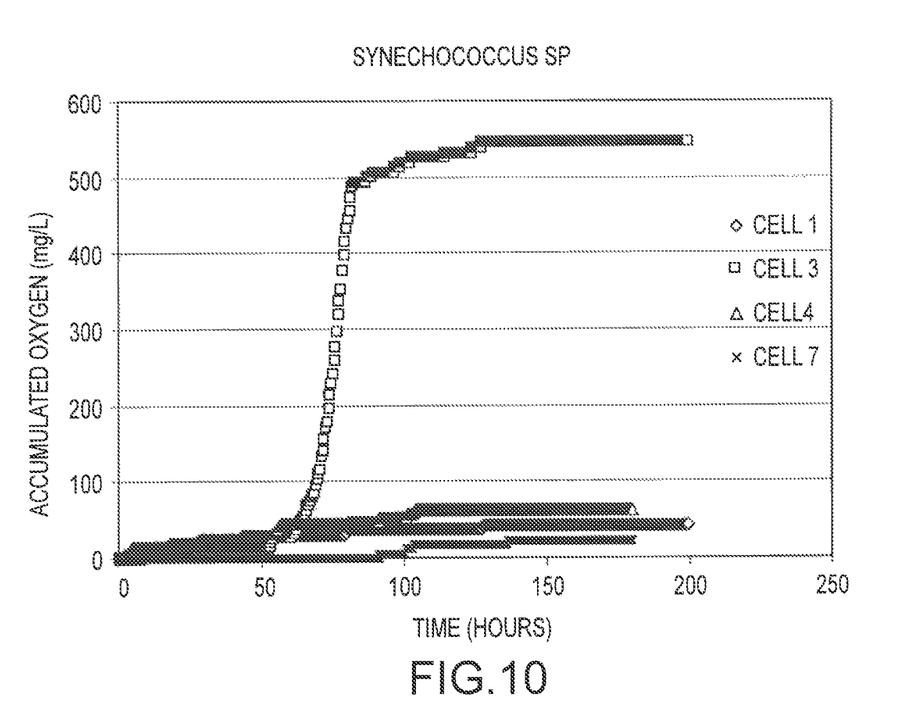
FIG. 10 depicts accumulated oxygen uptake from an experiment with *Synechococcus* sp. cells as a function of time.

FIG. 10 depicts accumulated oxygen (mg/L) uptake from an experiment with *Synechococcus* sp. cells as a function of time. Culture cells 1-3 contained growth medium with *Synechococcus* sp. Cells, whereas control cell 7 contained only DI water. The different result obtained for culture cell 3 vis-à-vis culture cells 1-2 was due to the higher level of light to which culture cell 3 was exposed. Again, this test demonstrates the capacity of *Synechococcus* sp. cells in the presence of light to generate local oxygen within an oxygen-deprived space.

Additional data was collected from in vivo experimentation using the right eye of fifteen rabbits, comprised of 3 groups: control, sham, and active (having an exemplary implantable ophthalmic device such as that described with reference to FIG. 5, referred to as "the oxygenation treated group").

A central retinal artery occlusion was induced for 90 min. In the sham and active groups, an implant was placed in the vitreous cavity for 30 min after the end of the occlusion. Oxygen readings were taken in all eyes before the occlusion, 30 min after implantation, and then at day 15. Baseline ERGs and final histology were also done.

Figure 11:
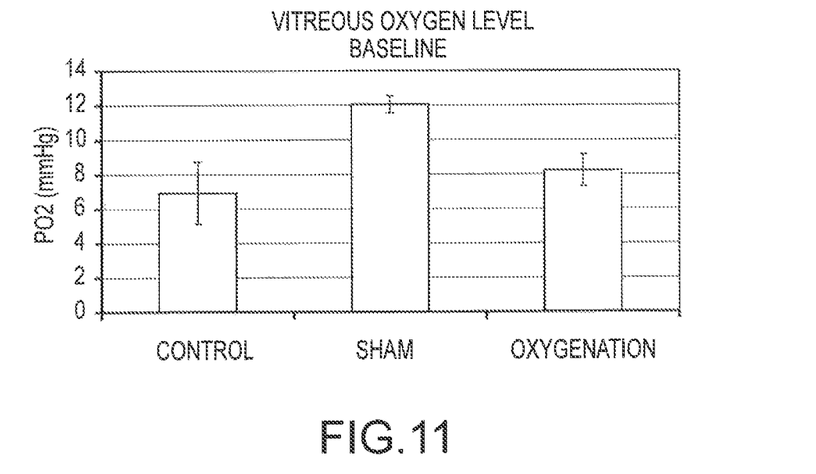
FIG. 11 illustrates vitreous oxygen levels for control, sham, and active groups at baseline, as part of in vivo experimentation conducted using an exemplary implantable ophthalmic device.
Figure 12:
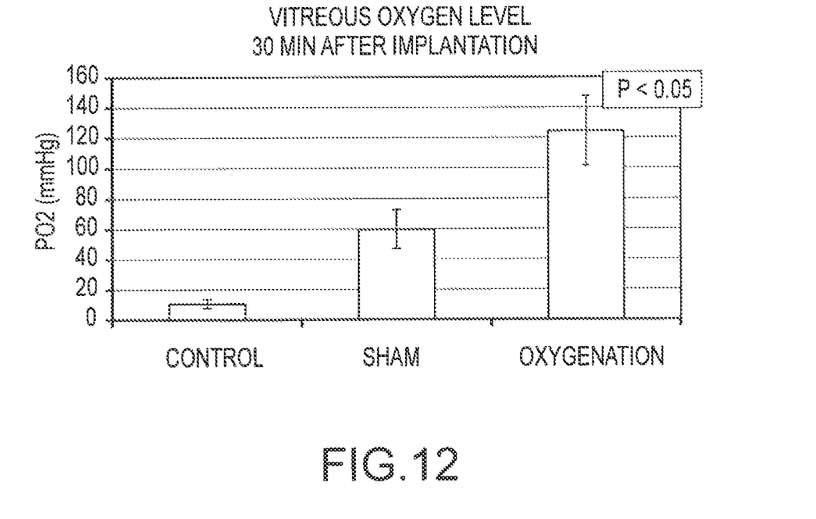
FIG. 12 illustrates vitreous oxygen levels for control, sham, and active groups at 30 minutes, as part of in vivo experimentation conducted using an exemplary implantable ophthalmic device.
Figure 13:
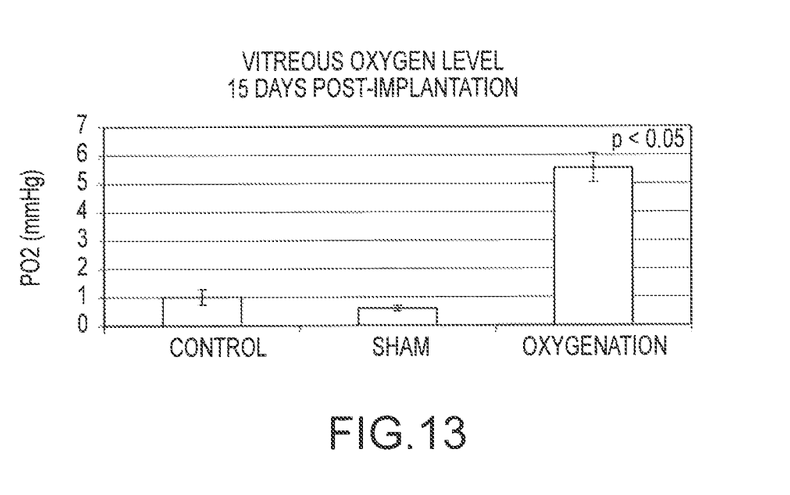
FIG. 13 illustrates vitreous oxygen levels for control, sham, and active groups at 15 days, as part of in vivo experimentation conducted using an exemplary implantable ophthalmic device.

FIG. 11 illustrates vitreous oxygen levels for each group at baseline, and demonstrates no statistical difference between groups. FIG. 12 illustrates vitreous oxygen levels for each group at 30 minutes after implantation, and demonstrates statistically significant higher levels of oxygen in the oxygenation treated group. FIG. 13 illustrates vitreous oxygen levels for each group at 15 days after implantation, and demonstrates statistically significant higher oxygen levels in the oxygenation treated group.

Figure 14:
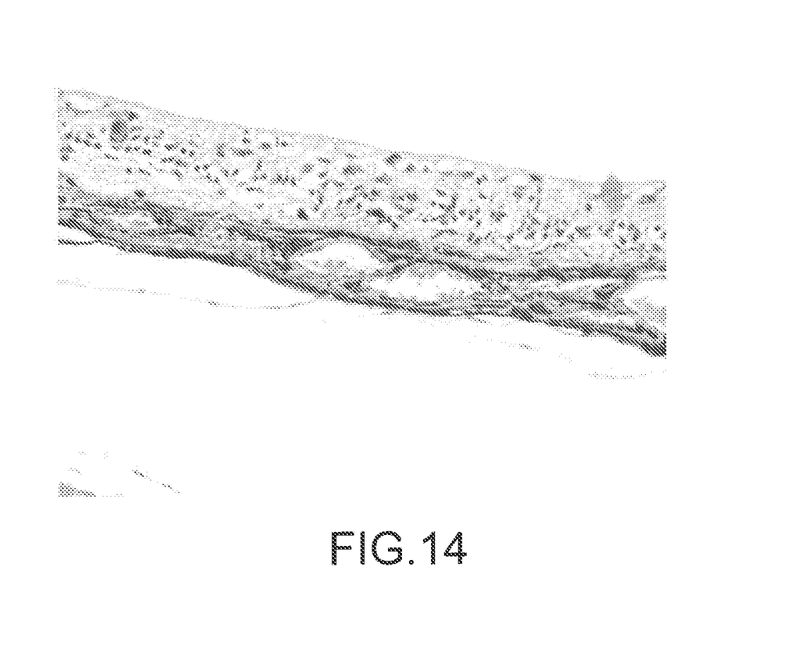
FIG. 14 illustrates retinal histology for the control and sham groups, as part of in vivo experimentation conducted using an exemplary implantable ophthalmic device.

The retinal histology illustrated in FIG. 14 demonstrates that both the sham and control eyes show marked decreased retinal thickness, with increased cellular vacuolization and disorganization. There is loss of the inner and outer nuclear layers, and loss of retinal photoreceptors. There is severe attenuation of the choriocapillaris.

Figure 15:
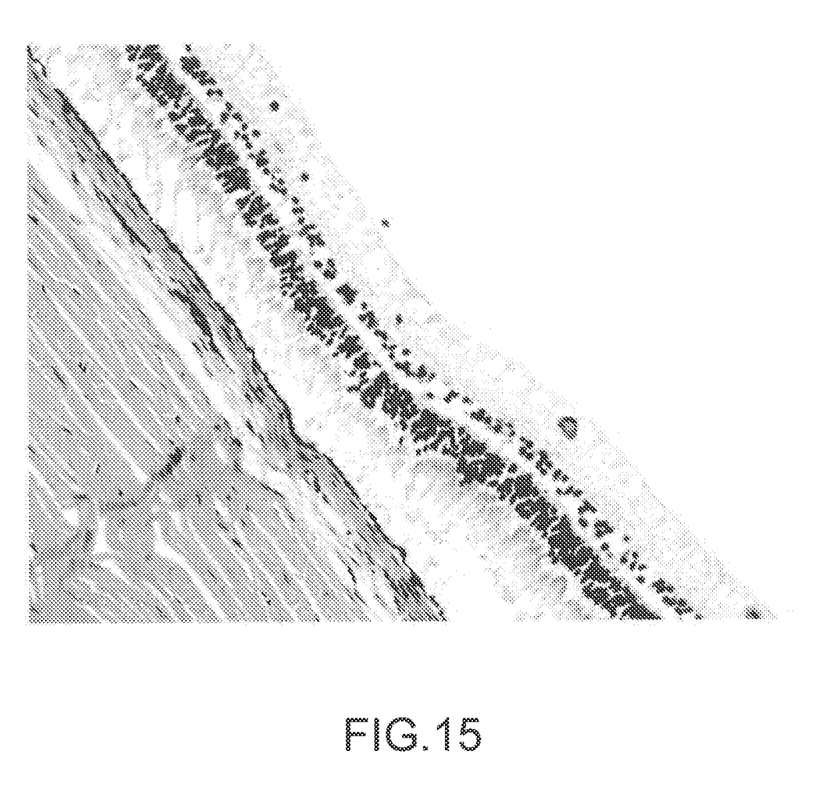
FIG. 15 illustrates retinal histology for the active group, as part of in vivo experimentation conducted using an exemplary implantable ophthalmic device.

In contrast, the retinal histology illustrated in FIG. 15 demonstrates that the oxygenation treated group show relatively normal retinal thickness and architecture.

Electroretinography was done on all eyes at baseline and at the end of 15 days. There was no difference in b-wave amplitude between the three groups at baseline. For the final ERGs, Scotopic b-wave amplitude was reduced in the control groups compared with the oxygenation treated group. Both the sham treatment and the no treatment groups demonstrated a statistically significant reduction of the final scotopic b-wave amplitude at 2 weeks from the baseline recordings, whereas the oxygenation treated group showed no statistically significant difference from the baseline recordings.

It will be apparent to those skilled in the art that various modifications and variations can be made in the present disclosure without departing from the spirit or scope of the disclosure. Thus, it is intended that the present disclosure cover the modifications and variations of this disclosure provided they come within the scope of the appended claims and their equivalents. For example, while exemplary embodiments have been described with regard to ischemic retinopathies, exemplary embodiments may apply more generally to other ischemias and/or chronic shortages of oxygen.

I claim:

1. An implantable ophthalmic device comprising:
    a shell comprising a porous membrane and a portion that is transparent;
    photosynthetic oxygenic bacteria encapsulated within the shell; and
    growth medium encapsulated within the shell.

2. The implantable ophthalmic device of claim 1, wherein the shell has one of the following shapes: spherical, cylindrical tubular, elongate tubular shape, or capsule.

3. The implantable ophthalmic device of claim 1, wherein the porous membrane comprises biologically inert reconstituted cellulose.

4. The implantable ophthalmic device of claim 1, wherein the porous membrane has an average pore size of about 13 kDa.

5. The implantable ophthalmic device of claim 1, wherein the porous membrane is configured to allow oxygen and carbon dioxide exchange.

6. The implantable ophthalmic device of claim 1, wherein the porous membrane is configured to prevent immune cells from reaching an interior of the implantable ophthalmic device.

7. The implantable ophthalmic device of claim 1, wherein the porous membrane is configured to prevent the photosynthetic oxygenic bacteria from migrating out of the implantable ophthalmic device.

8. The implantable ophthalmic device of claim 1, wherein the photosynthetic oxygenic bacteria is *Synechococcus* sp.

9. The implantable ophthalmic device of claim 1, wherein the porous membrane comprises biologically inert reconstituted cellulose, wherein the porous membrane has an average pore size of about 13 kDa, wherein the porous membrane is configured to allow oxygen and carbon dioxide exchange, wherein the porous membrane is configured to prevent immune cells from reaching an interior of the implantable ophthalmic device, and wherein the porous membrane is configured to prevent the photosynthetic oxygenic bacteria from migrating out of the implantable ophthalmic device.

\* \* \* \* \*